United States Patent
Bolster et al.

(10) Patent No.: US 9,486,003 B2
(45) Date of Patent: *Nov. 8, 2016

(54) HYPOCALORIC, HIGH PROTEIN NUTRITIONAL COMPOSITIONS AND METHODS OF USING SAME

(75) Inventors: Doug Bolster, Eden Prairie, MN (US); Zamzam Fariba Roughead, Plymouth, MN (US); Norman Alan Greenberg, New Hope, MN (US); Jennifer Mager, St. Louis, MO (US)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/805,795

(22) PCT Filed: Jun. 28, 2011

(86) PCT No.: PCT/US2011/042148
§ 371 (c)(1),
(2), (4) Date: Mar. 1, 2013

(87) PCT Pub. No.: WO2012/006074
PCT Pub. Date: Jan. 12, 2012

(65) Prior Publication Data
US 2013/0203664 A1  Aug. 8, 2013

Related U.S. Application Data

(60) Provisional application No. 61/359,179, filed on Jun. 28, 2010, provisional application No. 61/371,829, filed on Aug. 9, 2010, provisional application No. 61/447,155, filed on Feb. 28, 2011, provisional application No. 61/466,019, filed on Mar. 22, 2011.

(51) Int. Cl.
| | | |
|---|---|---|
| *A23L 1/29* | (2006.01) | |
| *A23L 1/302* | (2006.01) | |
| *A23L 1/304* | (2006.01) | |
| *A23L 1/305* | (2006.01) | |
| *A61K 31/59* | (2006.01) | |
| *A61K 31/7088* | (2006.01) | |
| *A61K 35/34* | (2015.01) | |
| *A61K 36/00* | (2006.01) | |
| *A61J 15/00* | (2006.01) | |

(52) U.S. Cl.
CPC ............... *A23L 1/296* (2013.01); *A23L 1/302* (2013.01); *A23L 1/304* (2013.01); *A23L 1/3055* (2013.01); *A23L 1/3056* (2013.01); *A61K 31/59* (2013.01); *A61K 31/7088* (2013.01); *A61K 35/34* (2013.01); *A61K 36/00* (2013.01); *A61J 15/00* (2013.01)

(58) Field of Classification Search
None
See application file for complete search history.

(56) References Cited

U.S. PATENT DOCUMENTS 5,723,446 A * 3/1998 Gray et al. ............. 514/5.5

FOREIGN PATENT DOCUMENTS

| BG | 548Y1 U | 8/1997 | |
|---|---|---|---|
| CN | 1257731 | 6/2000 | |
| CN | 1330881 | 1/2002 | |
| EP | 0614616 | 9/1994 | |
| GB | 2090115 | 7/1982 | |
| JP | 2002315548 | 10/2002 | |
| JP | 2006104147 | 4/2006 | |
| WO | WO 95 18618 | * 10/1995 | ............. A61K 38/00 |
| WO | WO 99/58001 | * 11/1999 | ............. A23L 1/305 |
| WO | WO9958001 | 11/1999 | |
| WO | WO 2004/103383 | * 12/2004 | ............. A23L 1/305 |
| WO | WO2004103383 | 12/2004 | |
| WO | WO 2005/110124 A1 | * 11/2005 | ............. A23L 1/305 |
| WO | WO2005110124 | 11/2005 | |
| WO | WO 2009/135959 A1 | * 11/2009 | ............. A23L 1/305 |
| WO | WO2009135959 | 11/2009 | |

OTHER PUBLICATIONS

NestleHealthScience "Products: Compleat Pediatric" (downloaded on Aug. 23, 2013 from http://www.nestlehealthscience.us/products/compleat%C2%AE-pediatric).*
Malone ("Enteral Formula Selection" A Review of Selected Product Categories Practical Gastroenterology (Jun. 2005) 44-74).*
Tremblay ("What Are Nucleotides and What Foods Can They Be Found in" (Jun. 15, 2011) downloaded Aug. 23, 2013 from http://www.livestrong.com/article/471632-what-are-nucleotides-and-what-foods-can-they-be-found-in/).*
Malone (Practical Gastroenterology (Jun. 2005) 44-74).*
Tremblay (Livestrong.com, "What are nucelotides and what foods can they be found in," Jun. 15, 2011).*
USDA (National Nutrient Database for Standard Reference—Chicken, downloaded from http://ndb.nal.usda.gov/ndb/foods/show/850fg=&man=&lfacet=&format=&count=&max=25&offset=&sort=&qlookup=chicken+breast on Jul. 8, 2014).*

(Continued)

*Primary Examiner* — Marcela M Cordero Garcia
*Assistant Examiner* — Mindy Newman
(74) *Attorney, Agent, or Firm* — K&L Gates LLP

(57) ABSTRACT

Nutritional compositions having reduced amounts of calories and high amounts of protein and methods of making and using the nutritional compositions are provided. The nutritional compositions may include a processed whole food component, a high amount of protein, and a reduced amount of calories in order to provide a patient with a pH-balanced formulation that includes the benefits of food bioactives beyond essential macro- and micronutrients without providing excessive energy. Methods of administering such nutritional compositions to patients in need of improved bone, muscle, neurological, immune, and/or overall health are also provided.

19 Claims, No Drawings

(56) References Cited

OTHER PUBLICATIONS

George Mateljan Foundation (2001, "Green Peas").*
Tremblay (Livestrong.com, "What are nucelotides and what foods can they be found in," Jun. 15, 2011 ).*
Malone (Practical Gastroenterology, Jun. 2005, 44-74).*
NestleHealthScience (Products: Compleat Pediatric, 2013).*
The Evanosky Foundation ("Pediatric G-Tube Formulas and Supplements" (Sep. 2008) downloaded from http://www.evanoskyfoundation.org/PDF%20Articles/G%020Tube%20Formulas%20092808.pdf on Jul. 8, 2014).*
NestleHealthScience, Products: Compleat Pediatric Reduced Calorie, 2014, downloaded from http://www.nestlehealthscience.us/products/Pages/Compleat%C2%AE-PEDIATRIC-REDUCED-CALORIE.aspx on Jul. 8, 2014.*
Self Nutrition Data, "Milk, whole, 3.25% milkfat" downloaded from http://nutritiondata.self.com/facts/dairy-and-egg-products/69/2 on Jan. 27, 2015).*
Dini et al, Invest Clin (Dec 2004) 45(4): 323-335; (English Abstract downloaded from http://www.ncbi.nlm.nih.gov/pubmed/15602899 on Jan. 27, 2015).*
Duncan ("Tube Feeding Associated Diarrhea," condensed chapter from Intestinal Failure, edited by Nightingale (2001), downloaded from http://www.oley.org/lifeline/diarrhea.html on Jan. 27, 2015).*
Malone (Practical Gastoenterology (Jun. 2005) 44-69).*
Dickerson (Nutrition (Mar. 2002)18(3):241-6).*
Of Tremblay ("What Are Nucleotides and What Foods Can They Be Found in" (Jun. 15, 2011) downloaded Aug. 23, 2013 from http://www.livestrong.com/article/471632-what-are-nucleotides-and-what-foods-can-they-be-found-in/).*
George Mateljan Foundation ("Green peas" (2001) downloaded on Aug. 23, 2013 from http://www.whfoods.com/genpage.php?tname=foodspice&dbid=55).*
Parrish (Practical Gastroenterology. (Sep. 2003) Nutritional Issues in Gastroenterology, Series #9, "Enteral Feeding: Dispelling Myths," pp. 33-50).*
Search Report for International Patent Application No. PCT/US2011/042148 mailed Dec. 2, 2011.
Yakagaku, 1991, pp. 923-930
Kagaku to seibutsu, 1990, pp. 238-245.
Mie igaku, 1984, vol. 27, pp. 528-530.
Japanese Office Action for Patent Application No. P2013-518567 dated Nov. 6, 2014.
Mexico Office Action for Application No. MX/a/2012/015080 dated Jan. 12, 2016, 4 pages.
Ensminger et al. "Elemental Diets (Semisynthetic Fiber-Free Liquid Diets)" Foods & Nutrition Encyclopedia, 2nd Edition, 1993, 5 pages.
Chinese Office Action for Application No. 201180032248.0 dated May 3, 2016, 18 pages.

* cited by examiner

HYPOCALORIC, HIGH PROTEIN NUTRITIONAL COMPOSITIONS AND METHODS OF USING SAME

CROSS REFERENCE TO RELATED APPLICATIONS

The present application is a National Stage of International Application No. PCT/US2011/042148, filed on Jun. 28, 2011, which claims priority to U.S. Provisional Patent Application No. 61/359,179, filed Jun. 28, 2010, U.S. Provisional Patent Application No. 61/371,829, filed Aug. 9, 2010, U.S. Provisional Patent Application No. 61/447,155, filed Feb. 28, 2011, and U.S. Provisional Patent Application No. 61/466,019, filed Mar. 22, 2011, the entire contents of which are being incorporated herein by reference.

SUMMARY

Nutritional compositions including whole foods are provided. Methods of making and using the nutritional compositions are also provided. In a general embodiment, the present disclosure provides hypocaloric, complete daily feeding, tube feed formulations including a processed whole food component, a source of vitamins or minerals and a source of protein that provides energy from protein in an amount from about 18% to about 35% of the total energy of the formulation.

In an embodiment, the processed whole food component may be selected from the group consisting of a processed fruit, a processed vegetable, a processed meat, a processed grain, or combinations thereof. In another embodiment the whole food component is not processed.

In an embodiment, the tube feed formulation has a caloric density from about 0.5 to about 0.8 kcal/ml.

In an embodiment, the protein is selected from the group consisting of dairy based proteins, plant based proteins, animal based proteins, artificial proteins, or combinations thereof. The dairy based proteins may be selected from the group consisting of casein, caseinates, casein hydrolysate, whey, whey hydrolysates, whey concentrates, whey isolates, milk protein concentrate, milk protein isolate, or combinations thereof. Plant based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, and any proteins derived from beans, buckwheat, lentils, pulses, single cell proteins, or combinations thereof. The animal based proteins may be selected from the group consisting of beef, poultry, fish, lamb, seafood, or combinations thereof.

In an embodiment, the tube feed formulation includes a prebiotic selected from the group consisting of acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof.

In an embodiment, the tube feed formulation includes a probiotic selected from the group consisting of probiotics include *Aerococcus*, *Aspergillus*, *Bacteroides*, *Bifidobacterium*, *Candida*, *Clostridium*, *Debaromyces*, *Enterococcus*, *Fusobacterium*, *Lactobacillus*, *Lactococcus*, *Leuconostoc*, *Melissococcus*, *Micrococcus*, *Mucor*, *Oenococcus*, *Pediococcus*, *Penicillium*, *Peptostrepococcus*, *Pichia*, *Propionibacterium*, *Pseudocatenulatum*, *Rhizopus*, *Saccharomyces*, *Staphylococcus*, *Streptococcus*, *Torulopsis*, *Weissella*, or combinations thereof.

In an embodiment, the tube feed formulation includes an amino acid selected from the group consisting of alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

In an embodiment, the tube feed formulation includes a fatty acid component of a fish oil selected from the group consisting of docosahexaenoic acid ("DHA"), eicosapentaenoic acid ("EPA"), or combinations thereof. DHA and EPA may also be derived from krill, algae, modified plants, flaxseed, walnut, etc. Certain fatty acids (e.g., 18:4 fatty acids) may also be readily converted to DHA and/or EPA.

In an embodiment, the tube feed formulation includes at least one phytonutrients. In an embodiment, the phytonutrients(s) are selected from the group consisting of flavanoids, allied phenolic compounds, polyphenolic compounds, terpenoids, alkaloids, sulphur-containing compounds, or combinations thereof. The phytonutrient may be, for example, a carotenoids, plant sterols, quercetin, curcumin, or limonin, or combinations thereof.

In an embodiment, the tube feed formulation includes a nucleotide. The nucleotide may be a subunit of deoxyribonucleic acid, a subunit of ribonucleic acid, polymeric deoxyribonucleic acid, polymeric ribonucleic acid, or combinations thereof.

In an embodiment, the tube feed formulation includes an antioxidant selected from the group consisting of astaxanthin, carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin C, vitamin E, zeaxanthin, or combinations thereof.

In an embodiment, the vitamins are selected from the group consisting of vitamin A, and precursors such as beta carotene, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, K1 and K2 (i.e MK-4, MK-7), folic acid, biotin, choline or combinations thereof.

In an embodiment, the minerals are selected from the group consisting of various salt forms of boron, calcium, chromium, copper, iodine, iron, magnesium, manganese, molybdenum, nickel, phosphorus, potassium, selenium, silicon, tin, vanadium, zinc, or combinations thereof.

In another embodiment, the present disclosure provides methods of making a complete daily feeding tube feed composition. The methods include combining a whole food component, a source of vitamins or minerals and a source of protein that provides energy from protein in an amount from about 18% to about 35% to form a mixture. The methods further include processing the mixture to form a tube feed composition that is a complete daily feeding. The processing may include blenderizing or liquefying and the whole food component may be a source of phytochemicals and/or nucleotides.

In an embodiment, the whole food component may be selected from the group consisting of a fruit, a vegetable, a meat, a grain, an herb, a spice, a flavoring, or combinations thereof.

In yet another embodiment, the present disclosure provides methods of improving the overall health of a tube fed pediatric patient having an underlying medical condition, including those long-term tube fed pateints. The methods include administering to a tube fed pediatric patient having an underlying medical condition a hypocaloric, complete daily feeding, tube feed formulation having a processed whole food component, a source of vitamins or minerals, and a source of protein that provides from about 18% to about 35% energy from protein. The underlying medical condition may be cerebral palsy, failure-to-thrive, neuromuscular disorders, brain injury, developmental delay, immunodeficiency, low bone density, pressure ulcers, chronic wounds, or combinations thereof.

In still yet another embodiment, the present disclosure provides methods of treating and/or preventing obesity or minimizing excessive fat-mass accretion in a long-term tube fed pediatric patient. The methods include administering to a tube fed pediatric patient that is obese, or at risk of becoming obese, a hypocaloric, complete daily feeding, tube feed formulation including a processed whole food component, a source of vitamins or minerals, and a source of protein that provides from about 18% to about 35% energy from protein.

In another embodiment, the present disclosure provides methods of promoting normal growth in a tube fed pediatric patient. The methods include administering to a tube fed pediatric patient in need of same a hypocaloric, complete daily feeding, tube feed formulation including a processed whole food component, a source of vitamins or minerals, and a source of protein that provides from about 18% to about 35% energy from protein.

In yet another embodiment, the present disclosure provides methods of maintaining metabolic homeostasis in a tube fed pediatric patient. The methods include administering to a patient in need of same a hypocaloric, complete daily feeding, tube feed formulation including a processed whole food component, a source of vitamins or minerals, and a source of protein that provides from about 18% to about 35% energy from protein.

In still yet another embodiment, the present disclosure provides methods of improving bone health in a tube fed pediatric patient on an anti-seizure medication. The methods include administering to a tube fed pediatric patient on an anti-seizure medication a hypocaloric, complete daily feeding, tube feed formulation including a processed whole food component, a source of vitamin D that provides at least 500 IU of vitamin D per 1 liter of the formulation or per 600 kcal, and a source of protein that provides from about 18% to about 35% energy from protein. The vitamin D should be administered per 1 liter of product, or per 600 kcal of the total composition.

In another embodiment, methods of reducing healthcare costs for a tube fed pediatric patient are provided. The methods include providing a hypocaloric, complete daily feeding, tube feed formulation including a processed whole food component, a source of vitamins or minerals, and a source of protein that provides from about 18 to about 35% energy from protein per day. The methods further include administering the tube feed formulation to a tube fed pediatric patient having an underlying medical condition that requires medical care. The administration of the tube feed formulation improves the underlying medical condition of the patient. In an embodiment, the underlying medical condition is selected from the group consisting of cerebral palsy, failure-to-thrive, neuromuscular disorders, brain injury, developmental delay, prolonged bed rest, immobilization, paraplegia/quadraplegia, immunodeficiency, low bone density, pressure ulcers, chronic wounds, or combinations thereof.

In still yet another embodiment, methods of improving the overall health of children are provided. The methods include administering to a child a tube feed formulation including a processed whole food component, a source of vitamins or minerals, and a source of protein that provides from about 1.6 to about 3.6 g protein per kg body weight per day, wherein the formulation provides the child with about 900 to about 1,100 kcal per day.

In an embodiment, the source of protein provides about 1.8 g protein per kg body weight. The source of protein may also provide about 3.5 g protein per kg body weight. The formulation may provide the child with about 1,000 kcal per day.

In another embodiment, methods of improving the overall health of pre-adolescents are provided. The methods include administering to a pre-adolescent a tube feed formulation including a processed whole food component, a source of vitamins or minerals, and a source of protein that provides from about 1.25 to about 2.75 g protein per kg body weight per day, wherein the formulation provides the pre-adolescent with about 1,100 to about 1,300 kcal per day.

In an embodiment, the source of protein provides about 1.35 g protein per kg body weight. The source of protein may also provide about 2.63 g protein per kg body weight. The formulation may provide the pre-adolescent with about 1,200 kcal per day.

An advantage of the present disclosure is to provide improved tube feed formulations.

Another advantage of the present disclosure is to provide improved nutritional compositions that comprise whole foods.

Yet another advantage of the present disclosure is to provide nutritional compositions that promote bone health.

Still yet another advantage of the present disclosure is to provide a nutritional compositions that preserves lean body mass and to minimize accretion of excessive fat mass.

Another advantage of the present disclosure is to provide nutritional compositions that maintain metabolic homeostasis.

Yet another advantage of the present disclosure is to provide nutritional compositions that treat and/or prevent pressure ulcers.

Yet another advantage of the present disclosure is to provide nutritional compositions that maintain bowel health.

Yet another advantage of the present disclosure is to provide nutritional compositions that improve and/or prevent feeding intolerance with tube feeding.

An advantage of the present disclosure is to provide nutritional compositions that improve the overall health of patients with cerebral palsy and/or other neuromuscular disorders.

Additional features and advantages are described herein, and will be apparent from the following Detailed Description and the figures.

DETAILED DESCRIPTION

As used herein, "about" is understood to refer to numbers in a range of numerals. Moreover, all numerical ranges herein should be understood to include all integer, whole or fractions, within the range.

As used herein the term "amino acid" is understood to include one or more amino acids. The amino acid can be, for example, alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

As used herein, "animal" includes, but is not limited to, mammals, which include but is not limited to, rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals that are capable of the effect exhibited or intended to be exhibited by the context of the passage.

As used herein, the term "antioxidant" is understood to include any one or more of various substances such as beta-carotene (a vitamin A precursor), vitamin C, vitamin E, and selenium) that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include astaxanthin, carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin C, vitamin E, zeaxanthin, or combinations thereof.

As used herein, "complete nutrition" includes nutritional products and compositions that contain sufficient types and levels of macronutrients (protein, fats and carbohydrates) and micronutrients to be sufficient to be a sole source of nutrition for the animal to which it is being administered to. Patients can receive 100% of their nutritional requirements from such complete nutritional compositions.

As used herein, "effective amount" is an amount that prevents a deficiency, treats a disease or medical condition in an individual or, more generally, reduces symptoms, manages progression of the diseases or provides a nutritional, physiological, or medical benefit to the individual. A treatment can be patient- or doctor-related.

While the terms "individual" and "patient" are often used herein to refer to a human, the invention is not so limited. Accordingly, the terms "individual" and "patient" refer to any animal, mammal or human having or at risk for a medical condition that can benefit from the treatment.

As used herein, non-limiting examples of fatty acid components of fish oils include docosahexaenoic acid ("DHA") and eicosapentaenoic acid ("EPA"). Additional sources of DHA and EPA include krill, plant sources of omega 3, flaxseed, walnut, and algae.

As used herein, "food grade micro-organisms" means micro-organisms that are used and generally regarded as safe for use in food.

As used herein, "incomplete nutrition" includes nutritional products or compositions that do not contain sufficient levels of macronutrients (protein, fats and carbohydrates) or micronutrients to be sufficient to be a sole source of nutrition for the animal to which it is being administered to. Partial or incomplete nutritional compositions can be used as a nutritional supplement.

As used herein, "long term administrations" are preferably continuous administrations for more than 6 weeks. Alternatively, "short term administrations," as used herein, are continuous administrations for less than 6 weeks.

As used herein, "mammal" includes, but is not limited to, rodents, aquatic mammals, domestic animals such as dogs and cats, farm animals such as sheep, pigs, cows and horses, and humans. Wherein the term "mammal" is used, it is contemplated that it also applies to other animals that are capable of the effect exhibited or intended to be exhibited by the mammal.

The term "microorganism" is meant to include the bacterium, yeast and/or fungi, a cell growth medium with the microorganism, or a cell growth medium in which microorganism was cultivated.

As used herein, the term "minerals" is understood to include boron, calcium, chromium, copper, iodine, iron, magnesium, manganese, molybdenum, nickel, phosphorus, potassium, selenium, silicon, tin, vanadium, zinc, or combinations thereof.

As used herein, a "non-replicating" microorganism means that no viable cells and/or colony forming units can be detected by classical plating methods. Such classical plating methods are summarized in the microbiology book: James Monroe Jay, et al., *Modern food microbiology*, 7th edition, Springer Science, New York, N.Y. p. 790 (2005). Typically, the absence of viable cells can be shown as follows: no visible colony on agar plates or no increasing turbidity in liquid growth medium after inoculation with different concentrations of bacterial preparations ('non replicating' samples) and incubation under appropriate conditions (aerobic and/or anaerobic atmosphere for at least 24 h). For example, bifidobacteria such as *Bifidobacterium longum*, *Bifidobacterium lactis* and *Bifidobacterium breve* or *lactobacilli*, such as *Lactobacillus paracasei* or *Lactobacillus rhamnosus*, may be rendered non-replicating by heat treatment, in particular low temperature/long time heat treatment.

As used herein, "normal bone growth" refers to the process by which childhood and adolescent bones are sculpted by modeling, which allows for the formation of new bone at one site and the removal of old bone from another site within the same bone. This process allows individual bones to grow in size and to shift in space. During childhood bones grow because resorption (the process of breaking down bone) occurs inside the bone while formation of new bone occurs on its outer (periosteal) surface. At puberty the bones get thicker because formation can occur on both the outer and inner (endosteal) surfaces. The remodeling process occurs throughout life and becomes the dominant process by the time that bone reaches its peak mass (typically by the early 20s). In remodeling, a small amount of bone on the surface of trabeculae or in the interior of the cortex is removed and then replaced at the same site. The remodeling process does not change the shape of the bone, but it is nevertheless vital for bone health. Modeling and remodeling continue throughout life so that most of the adult skeleton is replaced about every 10 years. While remodeling predominates by early adulthood, modeling can still occur particularly in response to weakening of the bone.

As used herein, a "nucleotide" is understood to be a subunit of deoxyribonucleic acid ("DNA"), ribonucleic acid ("RNA"), polymeric RNA, polymeric DNA, or combinations thereof. It is an organic compound made up of a nitrogenous base, a phosphate molecule, and a sugar molecule (deoxyribose in DNA and ribose in RNA). Individual nucleotide monomers (single units) are linked together to form polymers, or long chains. Exogenous nucleotides are specifically provided by dietary supplementation. The exogenous nucleotide can be in a monomeric form such as, for example, 5'-Adenosine Monophosphate ("5'-AMP"), 5'-Guanosine Monophosphate ("5'-GMP"), 5'-Cytosine Monophosphate ("5'-CMP"), 5'-Uracil Monophosphate ("5'-UMP"), 5'-Inosine Monophosphate ("5'-IMP"), 5'-Thymine Monophosphate ("5'-TMP"), or combinations thereof. The exogenous nucleotide can also be in a polymeric form such as, for example, an intact RNA. There can be multiple sources of the polymeric form such as, for example, yeast RNA.

"Nutritional products," or "nutritional compositions," as used herein, are understood to include any number of optional additional ingredients, including conventional food additives (synthetic or natural), for example one or more acidulants, additional thickeners, buffers or agents for pH adjustment, chelating agents, colorants, emulsifies, excipient, flavor agent, mineral, osmotic agents, a pharmaceutically acceptable carrier, preservatives, stabilizers, sugar, sweeteners, texturizers, and/or vitamins. The optional ingredients can be added in any suitable amount. The nutritional products or compositions may be a source of complete nutrition or may be a source of incomplete nutrition.

As used herein the term "patient" is understood to include an animal, especially a mammal, and more especially a human that is receiving or intended to receive treatment, as it is herein defined.

As used herein, "phytochemicals" or "phytonutrients" are non-nutritive compounds that are found in many foods. Phytochemicals are functional foods that have health benefits beyond basic nutrition, are health promoting compounds that come from plant sources, and may be natural or purified. "Phytochemicals" and "Phytonutrients" refers to any chemical produced by a plant that imparts one or more health benefit on the user. Non-limiting examples of phytochemicals and phytonutrients include those that are:

i) phenolic compounds which include monophenols (such as, for example, apiole, carnosol, carvacrol, dillapiole, rosemarinol); flavonoids (polyphenols) including flavonols (such as, for example, quercetin, fingerol, kaempferol, myricetin, rutin, isorhamnetin), flavanones (such as, for example, fesperidin, naringenin, silybin, eriodictyol), flavones (such as, for example, apigenin, tangeritin, luteolin), flavan-3-ols (such as, for example, catechins, (+)-catechin, (+)-gallocatechin, (−)-epicatechin, (−)-epigallocatechin, (−)-epigallocatechin gallate (EGCG), (−)-epicatechin 3-gallate, theaflavin, theaflavin-3-gallate, theaflavin-3'-gallate, theaflavin-3,3'-digallate, thearubigins), anthocyanins (flavonals) and anthocyanidins (such as, for example, pelargonidin, peonidin, cyanidin, delphinidin, malvidin, petunidin), isoflavones (phytoestrogens) (such as, for example, daidzein (formononetin), genistein (biochanin A), glycitein), dihydroflavonols, chalcones, coumestans (phytoestrogens), and Coumestrol; Phenolic acids (such as: Ellagic acid, Gallic acid, Tannic acid, Vanillin, curcumin); hydroxycinnamic acids (such as, for example, caffeic acid, chlorogenic acid, cinnamic acid, ferulic acid, coumarin); lignans (phytoestrogens), silymarin, secoisolariciresinol, pinoresinol and lariciresinol); tyrosol esters (such as, for example, tyrosol, hydroxytyrosol, oleocanthal, oleuropein); stilbenoids (such as, for example, resveratrol, pterostilbene, piceatannol) and punicalagins;

ii) terpenes (isoprenoids) which include carotenoids (tetraterpenoids) including carotenes (such as, for example, α-carotene, β-carotene, β-carotene, δ-carotene, lycopene, neurosporene, phytofluene, phytoene), and xanthophylls (such as, for example, canthaxanthin, cryptoxanthin, aeaxanthin, astaxanthin, lutein, rubixanthin); monoterpenes (such as, for example, limonene, perillyl alcohol); saponins; lipids including: phytosterols (such as, for example, campesterol, beta sitosterol, gamma sitosterol, stigmasterol), tocopherols (vitamin E), and omega-3, 6, and 9 fatty acids (such as, for example, gamma-linolenic acid); triterpenoid (such as, for example, oleanolic acid, ursolic acid, betulinic acid, moronic acid);

iii) betalains which include Betacyanins (such as: betanin, isobetanin, probetanin, neobetanin); and betaxanthins (non glycosidic versions) (such as, for example, indicaxanthin, and vulgaxanthin);

iv) organosulfides, which include, for example, dithiolthiones (isothiocyanates) (such as, for example, sulphoraphane); and thiosulphonates (allium compounds) (such as, for example, allyl methyl trisulfide, and diallyl sulfide), indoles, glucosinolates, which include, for example, indole-3-carbinol; sulforaphane; 3,3'-diindolylmethane; sinigrin; allicin; alliin; allyl isothiocyanate; piperine; syn-propanethial-S-oxide;

v) protein inhibitors, which include, for example, protease inhibitors;

vi) other organic acids which include oxalic acid, phytic acid (inositol hexaphosphate); tartaric acid; and anacardic acid; or vii) combinations thereof.

As used in this disclosure and the appended claims, the singular forms "a," "an" and "the" include plural referents unless the context clearly dictates otherwise. Thus, for example, reference to "a polypeptide" includes a mixture of two or more polypeptides, and the like.

As used herein, a "prebiotic" is a food substance that selectively promotes the growth of beneficial bacteria or inhibits the growth or mucosal adhesion of pathogenic bacteria in the intestines. They are not inactivated in the stomach and/or upper intestine or absorbed in the gastrointestinal tract of the person ingesting them, but they are fermented by the gastrointestinal microflora and/or by probiotics. Prebiotics are, for example, defined by Glenn R. Gibson and Marcel B. Roberfroid, *Dietary Modulation of the Human Colonic Microbiota: Introducing the Concept of Prebiotics*, J. Nutr. 1995 125: 1401-1412. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof.

As used herein, probiotic micro-organisms (hereinafter "probiotics") are food-grade microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. See, Salminen S, Ouwehand A. Benno Y.

et al., *Probiotics: how should they be defined?*, Trends Food Sci. Technol. 1999:10, 107-10. In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products. Non-limiting examples of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

As used herein, a "processed whole food" is a whole food that has been modified from its natural or prepared state and is in a state so that it can be placed into a tube feed formulation.

The terms "protein," "peptide," "oligopeptides" or "polypeptide," as used herein, are understood to refer to any composition that includes, a single amino acids (monomers), two or more amino acids joined together by a peptide bond (dipeptide, tripeptide, or polypeptide), collagen, precursor, homolog, analog, mimetic, salt, prodrug, metabolite, or fragment thereof or combinations thereof. For the sake of clarity, the use of any of the above terms is interchangeable unless otherwise specified. It will be appreciated that polypeptides (or peptides or proteins or oligopeptides) often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention include, but are not limited to, acetylation, acylation, ADP-ribosylation, amidation, covalent attachment of a flavanoid or a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol ("GPI") membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins" which refers to linear or non-linear polypeptides, consisting of alternating repeats of a peptide.

Non-limiting examples of proteins include dairy based proteins, plant based proteins, animal based proteins and artificial proteins. Dairy based proteins may be selected from the group consisting of casein, caseinates, casein hydrolysate, whey, whey hydrolysates, whey concentrates, whey isolates, milk protein concentrate, milk protein isolate, or combinations thereof. Plant based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, and any proteins derived from beans, buckwheat, lentils, pulses, single cell proteins, or combinations thereof. Animal based proteins may be selected from the group consisting of beef, poultry, fish, lamb, seafood, or combinations thereof.

All dosage ranges contained within this application are intended to include all numbers, whole or fractions, contained within said range.

As used herein, a "synbiotic" is a supplement that contains both a prebiotic and a probiotic that work together to improve the microflora of the intestine.

As used herein, the terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition, such as nitrogen imbalance or muscle loss. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition.

As used herein, a "tube feed" is a complete or incomplete nutritional product or composition that is administered to an animal's gastrointestinal system, other than through oral administration, including but not limited to a nasogastric tube, orogastric tube, gastric tube, jejunostomy tube ("J-tube"), percutaneous endoscopic gastrostomy ("PEG"), port, such as a chest wall port that provides access to the stomach, jejunum and other suitable access ports.

As used herein the term "vitamin" is understood to include any of various fat-soluble or water-soluble organic substances (non-limiting examples include vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, K1 and K2 (i.e. MK-4, MK-7), folic acid and biotin) essential in minute amounts for normal growth and activity of the body and obtained naturally from plant and animal foods or synthetically made, pro-vitamins, derivatives, analogs.

As used herein, "whole food" or "real food" is understood to mean a food typically ingested by an individual in a normal daily diet when the food is in its natural or prepared state as opposed to any reduced components of the food. For example, a whole food may include any known fruits, vegetables, grain, meats or sources of protein.

As used herein, "zoo-chemicals" refers to functional foods that have health benefits beyond basic nutrition, and are health promoting compounds that are found in animal sources.

Patients that are either inactive or fed one single diet for a significant amount of time are susceptible to metabolic disturbances that may result from a lack of variety or proper nutrient values in their diets. For example, long-term tube-fed patients may suffer from such disturbances. Although the basic nutritional needs of the patient may be met through tube feeding, current formulas for tube feeding are not optimized for maintenance of patient health over long time periods.

Patients who receive long-term tube feeds often remain on a single dietary source for weeks, months, or even years. Such long-term, tube fed patients may suffer from any number of health complications including, for example, bone, muscle, neurological, gastrointestinal and immune health disorders. The nutritional needs of such long-term, tube fed patients with these types of chronic diseases and complications will certainly differ from those requiring short-term tube feedings.

For example, cerebral palsy is a chronic, non-progressive motor disability that results from an injury to the developing brain early in life. Cerebral palsy is generally characterized by dysfunctions in motor coordination and muscle tone. Because these patients are often wheel-chair bound or have severe difficulty with ambulation, their energy needs are significantly lower than those of healthy children, but their protein needs are often higher to support growth, repair and anabolic functions. These children often require exclusive tube feeding. Although the feeding needs of long-term tube fed patients is different than short-term tube fed patients, the skilled artisan will appreciate that the present compositions may be used for either short or long-term tube fed patients, as well as patients receiving supplemental nutritional.

In another example, while the body's blood pH is fairly well maintained over time, primarily through regulation by the kidneys and lungs, dietary intake can significantly influence the body's acid/base balance. Hospitalized, institutionalized, and recovering patients may be at an increased risk of metabolic disturbances caused by poor renal and/or pulmonary function. As a result, the acid-base potential of the diet becomes increasingly important in maintenance of the patient's health, including musculoskeletal and immune health.

Upon ingestion and after metabolism, foods can be categorized as either more net acidic or more alkaline producing. Correlational human intake data suggests that diets higher in fruits and vegetables support a net alkaline environment to help maintain metabolic homeostasis. Conversely, acid producing diets have been found to negatively impact musculoskeletal health. Correction of low-grade metabolic acidosis through diet modification may help to preserve skeletal muscle mass and musculoskeletal status and improve the health of patients with a variety of pathological conditions including, for example, muscle loss. The manipulation of Phosphorus (P), Sodium (Na), Magnesium (Mg), Potassium (K) and Calcium (Ca) in complete nutritional formulas can serve to enhance net alkaline production in this manner.

Because long-term tube fed patients lack variation in their food sources they may be particularly susceptible to the effects of such acid-forming diets. Although the kidneys are efficient at neutralizing acids, long term exposure to high acid is believed to overwhelm the kidneys' capacity to neutralize acid and potential damage may occur. As a result, alkaline compounds that include, but are not limited to, calcium are used to neutralize these dietary acids (in the case of muscle, glutamine can act as a buffer). The most readily available source of calcium in the body is bone. One theory is that high acid diets may contribute to bone loss as the body mobilizes stored calcium to buffer metabolic acid. The hypothesis is that low acid diets may result in benefits that include attenuation of bone and muscle loss as well as maintaining renal health. See, Wachman, A., et al., *Diet and Osteoporosis*, Lancet, 1:958-959 (1968); see also, Frassetto L, et al., *Potassium Bicarbonate Reduces Urinary Nitrogen Excretion in Postmenopausal Women*, J. Clin. Endocrinol. Metab., 82:254-259 (1997).

Indeed, bone fractures are a significant problem in children with spastic quadriplegia due to many factors. Additionally, many children with cerebral palsy are taking multiple anticonvulsant medications for seizure control, and alterations in vitamin D and calcium metabolism are associated with some anticonvulsant use. See, Hahn, T. J. et al., *Effect of Chronic Anticonvulsant Therapy on Serum 25-Hydroxycalciferol Levels in Adults*, The New England J. of Med., pp. 900-904 (Nov. 2, 1972). See also, Hunter, J. et al., *Altered Calcium Metabolism in Epileptic Children on Anti-convulsants*, British Medical Journal, pp. 202-204 (Oct. 23, 2971). See also, Hahn, T. J. et al., *Phenobarbital-Induced Alterations in Vitamin D Metabolism*, J. of Clinical Investigation, Vol. 51, pp 741-748 (1972). Although the influence of anticonvulsant medication on vitamin D status is not completely clear, it is apparent that non-ambulatory children are at increased risk for bone fractures.

Studies have shown that medications to control seizures, such as phenobarbital and Dilantin, can alter the metabolism and the circulating half-life of vitamin D. Research has also suggested that patients on at least two anti-seizure medications who are institutionalized and, therefore, not obtaining most of their vitamin D requirement from exposure to sunlight, increase their vitamin D intake to approximately 25 μg (1,000 IU)/day to maintain their serum 25(OH)D levels within the mid-normal range of 25 to 45 ng/ml (62.5 to 112.5 nmol/liter). It is thought that this should prevent the osteomalacia and vitamin D deficiency associated with anti-seizure medications.

In yet another example, patients, and especially children, with cerebral palsy and neuromuscular disorders are also frequently at risk of developing pressure ulcers or chronic wounds and, as such, may require special diets. Individuals that are susceptible to chronic wounds include, for example, those with prolonged immobilization, bed and chair bound and/or experiencing incontinence, those that are experiencing protein-energy malnourishment, immunosuppressed, or those with neurological, traumatic or terminal illnesses, or those with circulatory or sensory deficits. See, Agency for Health Care Policy and Research, 1992, 1994. Receiving adequate nutrition plays a key role in prevention and treatment of such chronic wounds.

For example, specific nutrients such as, for example, protein, vitamin A, vitamin C, vitamin E, zinc and arginine can play a role in reducing the risk of developing pressure ulcers, particularly if a deficiency is suspected. Adequate hydration also plays a significant role in reducing the risk of developing pressure ulcers. Indeed, it has been reported that incidence of pressure ulcer development was lower in a group receiving additional protein, arginine, vitamin C and zinc when compared to a control group (13% versus 72%). See, Neander, et al., *A specific nutritional supplement reduces incidence of pressure ulcers in elderly people*, Numico Research, www.numico-research.com.

Once a chronic wound or pressure ulcer has developed, various nutrients play an important role in healing, with specific nutrients having an impact at different phases of the process. For example, Table 1 below demonstrates the key nutrients that impact different phases of wound healing. As is shown in Table 1, certain vitamins, minerals and amino acids are present at the different phases of wound healing.

TABLE 1

| Phase | Process | Key Nutrients |
|---|---|---|
| Phase I: Inflammation | Wound exudation Fibrin clot formation | Vitamin C Vitamin E Selenium Arginine Cysteine Methionine |
| Phase II: Proliferation | Angiogenesis Fibroblast proliferation Collagen synthesis Wound matrix formation and epithelialization | Vitamin A Vitamin C Thiamin Pantothenic acid Zinc Manganese |
| Phase III: Maturation and Remodeling | Collagen cross linkage Wound contraction Tensile strength development | Vitamin A Vitamin C Zinc Copper Manganese |

There are also significant health economic implications with prevention of pressure ulcer development or progression. For example, the average healing times for pressure ulcers are longer at later stages of the ulcers, with Stage III and Stage IV ulcers requiring substantially longer treatment than Stage II. In a UK cost of illness study, it is clear that there are increased treatment costs with increased severity of pressure ulcers. See, Bennett G, et al., *The cost of pressure ulcers in the UK, Age and Ageing*, 33: 230-235 (2004). In another study, it was shown that Stage III and Stage IV pressure ulcers cost substantially more to treat than Stage II pressure ulcers. See, Xakellis G C, et al., *The cost of healing pressure ulcers across multiple health care settings*, Adv. Wound Care, 9:18-22 (1996). These significant costs are shown below in Table 2.

TABLE 2

| Stage | Total Treatment Cost per Pressure Ulcer Including Hospital Stay Mean (SD) | Treatment Cost per Pressure Ulcer Excluding Hospital Stay Mean (SD) | Hospitalization Cost per Pressure Ulcer |
|---|---|---|---|
| Stage I (n = 37) | $1,119 (4,234) | $443 (581) | $ 676 |
| Stage III and IV (n = 8) | $10,185 (27,635) | $700 (831) | $9,485 |
| All ulcers (n = 45) | $2731 (12,184) | $489 (629) | $2,242 |

More general still, there are many costs that must be taken into consideration for a pediatric patient on a tube feeding regime. Any underlying medical condition such as, for example, cerebral palsy, failure-to-thrive, neuromuscular disorders, brain injury, developmental delay, immunodeficiency, low bone density, chronic wounds, etc. may require medical care in a hospital or other medical facility. Alternatively, many of these conditions may also require, or allow supplementation of hospital visits with, home medical care. In either situation, daily feedings of a tube fed pediatric patient may include costs for the tube feed formula, costs for use of equipment to administer feedings, costs for health care personnel to administer feedings, costs for secondary health monitoring equipment, costs for doctor visits, etc. As discussed above with respect to pressure ulcers, a skilled artisan will appreciate that these costs will increase with increasing severity of the underlying medical condition.

As such, it would be beneficial for a pediatric tube fed patient, or the caretakers of the pediatric patient, to be able to reduce the frequency of medical visits, hospital stays, frequency of feedings, etc. in order to reduce healthcare costs. For example, it is known that pediatric tube fed patients commonly experience an impedance to normal growth because the patients are typically sedentary and not consuming all necessary micro- and macronutrients that are found in non-tube-fed meals. If the pediatric patient were administered a tube feed formulation, however, that provided all necessary micro- and macronutrients, higher amounts of protein and lower calories, for example, the tube fed pediatric patient may be able to experience an improved health status by minimizing excessive weight gain and/or excessive adipose tissue. Thus, administration of such a tube feeding may reduce medical costs associated with the pediatric patients condition as well as reduce the number of nutritional modulars (i.e. protein, fiber, micronutrients) which are typically "added back" to diluted 1.0 kcal formulas.

Based on the above discussions, it is clear that long-term tube feeding can cause any number of primary or secondary health concerns. Over time, if tube-feed formulas provided to patients having similar health complications to those described above do not provide all dietary constituents necessary to meet the patient's physiological needs, the cumulative day-after-day nutritional inadequacy (or differences from a natural, varied and balanced real food diet) may have gradual and detrimental side-effects on the patient's wellbeing and, therefore, clinical outcome.

Accordingly, the present disclosure is directed to nutritional products and compositions that provide these patients with sufficient volume, increased protein and higher levels of certain micronutrients and macronutrients without providing excessive energy. Higher protein is required to support anabolic functions, preserve lean body mass and maintain nutritional adequacy. The hypocaloric formulation is critical to deliver fewer calories to patients with extremely limited to almost no physical mobility as the nutrition provided must manage weight gain without compromising musculoskeletal health. Additionally, other dietary constituents may be provided in the nutritional products and compositions that are conditionally essential (e.g., nucleotides) or are otherwise important for wellbeing (e.g., phytochemicals) of the patient.

The nutritional composition can be administered to an individual having a preexisting medical condition, or at risk of developing a medical condition. As discussed above, the medical conditions may include, for example, cerebral palsy, failure-to-thrive, neuromuscular disorders, brain injury, developmental delay, immunodeficiency, low bone density, pressure ulcers, chronic wounds, or combinations thereof. The nutritional composition can be a formulation designed for any mammal such as a human or an animal. In an embodiment, the nutritional composition is a tube-feed formulation.

While the present nutritional compositions may be administered to any patient population, in an embodiment, the nutritional compositions are administered to a pediatric patient having, or at risk of developing, any of the above-mentioned medical conditions. Age ranges for different classes of pediatric patients can vary widely. As used herein, a "toddler" will be considered to be a pediatric patient that is between the age ranges of 2 and 5 years. The weight range of an toddler may be from about 30 kg to about 45 kg. the toddler may weigh about 36 kg. As used herein, a "child" will be considered to be a pediatric patient that is between the age ranges of 5 and 8 years. The weight range of a child may be from about 50 kg to about 60 kg. The child may weigh about 55 kg. As used herein, a "pre-adolescent" will be considered to be a pediatric patient that is between the age ranges of 8 and 13 years. The weight range of a pre-teen may be from about 80 kg to about 85 kg. The pre-teen may weigh about 88 kg.

The benefit of the present macronutrient distribution is support of growth while minimizing excessive weight gain, accretion of central adiposity and associated negative health effects. Central adiposity has been associated with insulin resistance and low grade inflammation, thus is it possible that provision of low energy, high protein diets to growing children with low physical activity will prevent the insulin resistance thus permitting more effective insulin activity and thus anabolism. High protein diets have been shown to modulate secretion of anabolic hormones such as growth hormone. See, Clarke, et al., *Effect of high proteinfeed supplements on concentrations of growth hormone ("GH"), insulin-like growth factor-I ("IGF-I") and IGF-binding protein-3 in plasma and on the amounts of GH and messenger RNA for GH in the pituitary glands of adult rams*, J. Endocrinol. 138 (3):421-427 (1993). See, also, J. R. Hunt, et al., *Dietary protein and calcium interact to influence calcium retention: a controlled feeding study*, Am. J. Clin. Nutr. 89 (5):1357-1365 (2009). See, also, G. Blanchard, et al., *Rapid weight loss with a high-protein low-energy diet allows the recovery of ideal body composition and insulin sensitivity in obese dogs*, J. Nutr. 134 (8 Suppl):2148S-2150S (2004).

These benefits are particularly important during rapid growth as the growth hormone axis has been shown to be associated with chronic diseases later in life. Therefore modulation of the growth hormone axis (including IGF-1) will benefit the clinical outcome of the patient both in the short term and also in later years. This can lead to significant improvement in quality of life but also in positive health economic outcomes. See, J. M. Kerver, et al., *Dietary predictors of the insulin-like growth factor system in adolescent females: results from the Dietary Intervention Study in Children (DISC)*, Am. J. Clin. Nutr. 91 (3):643-650 (2010).

The nutritional compositions may be administered as a bolus or a continuous tube feeding. In an embodiment, the nutritional compositions are administered as a bolus since it maximizes the physiological response to the feeding occasion. This method provides complete nutrition to a pediatric population since a concentrated dose of protein is delivered at each feeding. This concentrated provision of protein is essential to increasing plasma amino acids (e.g., leucine), stimulating protein synthesis, and attaining a net positive protein balance. This anabolic state post-feeding is required to optimize growth though the accrual of lean body mass and linear bone growth (accrual of bone mineral density). The mechanism is related to the above mentioned increase in serum leucine as well as anabolic endocrine response including the stimulation of the insulin-IGF-1-GH axis leading to increased uptake and bio-utilization of substrates for musculoskeletal development (thus, leading to reduced accumulation of visceral adiposity). In an embodiment, a complete feeding of the present nutritional compositions would be about 1000 ml for a pediatric patient that is from 1 to 13 years of age. Children older than age 13 and adults may benefit from such a formula but caloric requirements along with macro-micronutrients needs should be evaluated to ensure optimal delivery of nutrition.

Physiological feeding also includes introduction of variety into the growing child's diet. The idea includes bolus feeding which resembles the breakfast, lunch, dinner, snack pattern in which an enteral formulation is designed to include a variety of food components representative of a varied, mixed, cycle menu diet. The variety of food in the menu cycle may be further diversified by including ethnic food while enhancing the phytonutrient profile of the product from various fruits, vegetables, herbs or spices. This regimen incorporates benefits of real food beyond basic nutrients and may provide a source of phyto- and zoo-chemicals with health benefits. The benefits include, but are not limited to, powerful oxidative stress modulation leading to reduced insulin resistance and thus increased bio-utilization leading to accrual of lean body mass and buffering of net acid excretion leading to optimal linear growth and accrual of higher quality bone mass.

In an embodiment, tube feed formulations of the present disclosure include a whole food, or a real food, component. Whole foods contain beneficial food constituents in addition to the well-recognized macronutrients, vitamins and minerals. Several of these food constituents include phytochemicals and nucleotides, which provide several benefits to a patient on a long-term tube feeding diet.

Phytochemicals are non-nutritive compounds that are found in many fruits and vegetables, among other foods. There are thousands of phytochemicals that can be categorized generally into three main groups. The first group is flavonoids and allied phenolic and polyphenolic compounds. The second group is terpenoids, e.g., carotenoids and plant sterols. The third group is alkaloids and sulfur containing compounds. Phytochemicals are active in the body and, in general, act similarly to antioxidants. They also appear to play beneficial roles in inflammatory processes, clot formation, asthma, and diabetes. Researchers have theorized that to receive the most benefit from consumption of phytochemicals, they should be consumed as part of whole foods, because of the complex, natural combination and potentially synergistic effects. This may partially explain the health benefits associated with consumption of whole fruits and vegetables. Increased intake of fruits and vegetables is associated with reduced risk of many chronic diseases. In order to enhance the phytochemical profile of the present nutritional compositions, in an embodiment, the compositions include various fruits and vegetables containing these compounds.

As a component of adenosine triphosphate and associated molecules, nucleotides are also necessary for energy metabolism. Demand for nucleotides is highest in tissues with rapid cell turnover such as the gut and immune cells. Nucleotides can be obtained through dietary intake and also through the salvage pathway. Endogenous synthesis of nucleotides, although a high energy requiring process, appears to be sufficient in healthy individuals. However, the need for exogenous (dietary source) nucleotides occurs during situations of growth or stress, e.g., gut injury, sepsis, and immune challenge. See, Kulkarni et al., *The Role of Dietary Sources of Nucleotides in Immune Function: A Review*, Journal of Nutrition, pp. 1442S-1446S (1994). Several segments of the population on long-term tube feeds (elderly, pediatric populations, sedentary, bedridden and those with wounds) may particularly benefit from exogenous nucleotides. Decreased activity or a sedentary lifestyle, which is common in long-term tube fed patients, is associated with impaired immune function and altered gut function.

Although endogenous synthesis constitutes a major source of nucleotides, nucleotides can also be obtained in the form of nucleoproteins naturally present in all foods of animal and vegetable origin including, for example, animal protein, peas, yeast, beans and milk. Further, concentrations of RNA and DNA in foods are dependent on cell density. Thus, meat, fish and seeds have higher nucleotide content than milk, eggs and fruits. Consequently, organ meats, fresh seafood, and dried legumes are rich food sources. However, tube feeds by design are highly refined and do not contain nucleotides. Thus, nucleotides have been added to correct potential alterations in normal gut and immune function.

As mentioned above, and in addition to bone specific effects, human correlational data suggests that dietary intake of fruits and vegetables support a net alkaline environment which can help regulate metabolic homeostatis. This net alkaline state has been associated with an enhanced preservation of lean body mass, at least in older individuals. See, Dawson-Hughes B, et al., *Alkaline diets favor lean tissue mass in older adults*, Am J Clin Nutr. March; 87(3):662-5 (2008). Thus, the manipulation of Phosphorus (P), Sodium (Na), Magnesium (Mg), Potassium (K) and Calcium (Ca) in complete nutritional formulas can serve to enhance net alkaline production to further minimize endogenous skeletal muscle proteolysis as well as preserve lean body mass.

The cell energy charge has been proposed as an important control for the cell to favor either anabolic or catabolic processes. Cell energy charge has been defined Energy charge=(ATP+½ ADP)/(ATP+ADP+AMP) [where ATP, ADP, and AMP signify adenosine 5'-triphosphate, -diphosphate, and -monophosphate, respectively]. Metabolic stress, nutritional stress, or both may result in a loss of nucleotides from the adenylate pool and become conditionally essential under these conditions. The maintenance of the cell energy charge can attenuate the upregulation of catabolic processes resulting from metabolic stress, nutritional stress, or both, which includes protein breakdown.

AMP Protein Kinase ("AMPK") is a protein that serves as a cell energy charge sensor that responds to ATP/AMP as well phosphocreatine/creatine ("PCr"/"Cr") changing ratios for the prioritization of cellular processes based on available energy. Specifically, AMPK can target the translational control of skeletal muscle protein synthesis as well as upregulate the ubiquitin proteosome pathway.

Additionally, nucleotides can be beneficial in the nutritional management of pressure ulcer by improving the resistance to infection at the wound site. Chronic nucleotide supplementation may counteract the hormonal response associated with physiological stress, resulting in an enhanced immune response.

Extensive experimentation on the influence of dietary nucleotides on lymphocyte function and cellular immunity in rodent models has also been conducted. Evidence exists to assert that the absence of dietary nucleotides does significantly decrease specific and non-specific immune responses. Findings include decreased maturation and proliferation of lymphoid cells in response to mitogens, decreased resistance to bacterial and fungal infection, and increased allograft survival.

Lymphocyte differentiation and proliferation can be stimulated by specific nucleosides and, in turn, nucleotide metabolism may be influenced by stages of lymphocyte activation and function. Furthermore, de novo synthesis and salvage of purines and pyrimidines is increased in stimulated lymphocytes. In support, an established marker for undifferentiated T-cells, terminal deoxynucleotidyl transferase ("TdT"), has been identified in undifferentiated bone marrow and thymocytes of rodents fed diets devoid of nucleotides.

In vitro and in vivo studies of rodents on nucleotide free diets have demonstrated suppressed cell-mediated immune responses. Splenic lymphocytes from nucleotide free hosts evidenced significant decreases in proliferate response to mitogens, decreased interleukin-2 ("IL-2") production and lower levels of IL-2 receptor and Lyt-1 surface markers. IL-2 is a growth factor for lymphocytes, while Lyt-1 is a marker of helper-inducer T-cell immunity. Delayed cutaneous hypersensitivity was also lower.

These responses were largely reversed with additions of RNA or uracil, suggesting a formidable role for pyrimidines and/or limited capacity for their salvage. Furthermore, dietary nucleotides were shown to reverse lost immune response secondary to protein-calorie malnutrition more so than calories and protein alone. However, this reversal was limited to pyrimidines.

Investigations of the role of nucleotides in bacterial and fungal infection have also revealed increased resistance. Rodents on nucleotide containing diets demonstrated significant resistance to intravenous challenge of *Staphylococcus aureus* compared to those on nucleotide free diets. A decreased ability to phygocytose *S. aureus* was observed. Moreover, decreased survival times were observed in rodents on a nucleotide free diet after similar challenge with *Candida albicans*. Additions of RNA or uracil, but not adenine were shown to increase survival time.

The immunosuppressive effects of nucleotide free diets have also produced prolonged cardiac allograft survival in rodents as well as synergistic immunosuppression with cyclosporine A. These findings evidence influence on T-helper cell numbers and function. Various mechanisms of action have been proposed to explain these findings. Restriction of exogenous nucleotides is believed to influence the initial phase of antigen processing and lymphocyte proliferation via action on the T-helper-inducer as evidenced by increased levels of TdT in primary lymphoid organs. This is also suggestive of suppression of uncommitted T-lymphocyte response. Also, nucleotide restriction may cause arrest of T lymphocytes in the G phase of the cell cycle, thus inhibiting transition of lymphocytes to the S phase to illicit necessary immunological signals. Nucleotide restriction may also lower the cytolytic activity of natural killer ("NK") cells and lower macrophage activity.

Dietary or Exogenous nucleotides may also modulate T-helper cell mediated antibody production. A review of studies investigating nucleotide actions on humoral immune response identified effects in in vitro and in vivo animal models as well as in vitro actions in human systems. In vitro findings in splenic rodent cells primed with T-cell-dependent antigens displayed significant increases in the number of antibody producing cells in yeast RNA containing cultures. RNA additions to normal strains demonstrated similar results and were nullified by T-cell depletion. Thus, the antibody did not increase in response to T-cell independent antigens or polyclonal B cell activation. The specific antibody response of yeast RNA was attributed to nucleotides.

Immunoglobulin production has also been shown to increase in in vitro adult human peripheral blood mononuclear cell in response to T-cell dependent antigen and stimuli. Specifically, this involved increased immunoglobulin M ("IgM") and G ("IgG") production. IgM production increased in the functionally immature umbilical cord mononuclear cells in response to T-cell dependent stimuli as well.

Accordingly, in a state of nucleotide deficiency, incorporated dietary nucleotides could potentially exert similar immune effects in vivo. Antibody response to T-cell dependent antigen was suppressed in rodents maintained on nucleotide diets for prolonged periods, and immune function was rapidly restored with nucleotide supplementation. However, the mixture used for supplementation showed no effect on in vitro antibody production to antigen-dependent antigens suggestive of nucleotide effects on local, specific immune response. In addition, significant increases in the numbers of antigen-specific immunoglobulin-secreting cells were observed in rodent splenic cells in the presence of nucleotides. Additions of AMP, GMP or UMP have also resulted in increased IgG response in rodents. GMP was also shown to increase IgM response. Studies in preterm infants on nucleotide supplemented formulas have revealed increased circulating levels of IgM and IgA in the first three months of life as well as higher concentrations of specific IgG against α-casein and β-lactoglobulin in the first month of life. Specific IgG levels to low response antigens may also increase in normal infants receiving dietary nucleotide containing formulas.

Mechanistically, in vitro and in vivo observations are thought to involve nucleotide effects on T-helper-cells at antigen presentation, modulations via interactions with cell surface molecules of T-cells, suppressed nonspecific activation of T-cells in response to antigen stimulus, and increased specific antibody response mediated through resting T-cells. Therefore, dietary nucleotides may favor the balance of T-cell differentiation to T-helper-2-cells which are primarily involved in B-cell response. Thus, it is clear that nucleotides, as well as phytochemicals, can present several physiological benefits to patients having any of the above-mentioned conditions.

The skilled artisan will appreciate that any known fruits and vegetables may be used in the present nutritional compositions, so long as the fruits and vegetables are a source of phytochemicals and/or nucleotides. Further, the skilled artisan will also appreciate that the fruits and/or vegetables may be provided in any amounts effective to provide the patient with a sufficient amount of phytochemicals and/or nucleotides to achieve the advantages described above.

Although the known fruits and vegetables may provide a small amount of nucleotides, the primary benefit derived from nucleotides will be obtained by adding additional sources of exogenous nucleotides. In an embodiment, certain meats may serve as a source of exogenous nucleotides. For example, the nutritional compositions of the present disclosure include nucleotides in an amount of at least about 10 mg/100 kcal. In an embodiment, the nutritional compositions include from about 13 mg/100 kcal to about 19 mg/100 kcal nucleotides. In an embodiment, the nutritional compositions provide about 16 mg/100 kcal nucleotides. In an embodiment, fruits and vegetables are the sole source of nucleotides. In an embodiment, fruits and vegetables are a partial source of nucleotides.

Similarly, the nutritional compositions of the present disclosure include fruits and vegetables as a source of phytochemicals. In an embodiment, the nutritional compositions include an effective amount of phytochemicals.

Fruits included in the present nutritional compositions may include any known fruit such as, but not limited to, apples, bananas, coconut, pear, apricot, peach, nectarines, plum, cherry, blackberry, raspberry, mulberry, strawberry, cranberry, blueberry, grapes, grapefruit, kiwi, rhubarb, papaya, melon, watermelon, pomegranate, lemon, lime, mandarin, orange, tangerine, guava, mango, pineapple, etc. Similarly, vegetables may include any known vegetable such as, but not limited to, algae, amaranth, arugula, brussels sprouts, cabbage, celery lettuce, radicchio, water cress, spinach mushrooms, green beans, green peas, beans, tomato, beets, carrots, potatoes, radish, rutabaga, sea weed, turnips, etc.

As mentioned above, nutritional compositions in accordance with the present disclosure have high amounts of protein. High amounts of protein are required to support anabolic functions, preserve lean body mass and maintain nutritional adequacy. In an embodiment, the nutritional compositions comprise a source of protein. The protein source may be dietary protein including, but not limited to animal protein (such as milk protein, meat protein or egg protein), vegetable protein (such as soy protein, wheat protein, rice protein, and pea protein), or combinations thereof. In an embodiment, the protein is selected from the group consisting of whey, chicken, corn, caseinate, wheat, flax, soy, carob, pea or combinations thereof. In another embodiment, the protein is pea protein or pea protein isolate.

In an embodiment, vegetable proteins will be included to further enhance the net alkaline profile of the formula and increase the variety of macronutrient sources of mimic a real food diet while delivering high quality protein blends that provide the essential nutritional requirements for supporting growth and development. Based on the nutritional profile of specific vegetable proteins (e.g., pea protein isolate) there are limitations in the amount of vegetable protein sources that can be included in a formula. For example, the amino acid profile of pea protein includes all of the indispensable amino acids. Pea protein is relatively rich in arginine, but limiting in the sulphur-containing amino acids, methionine, and cysteine. However, it is possible, for example, to blend pea protein isolates with a complete protein source (such as milk protein or complete vegetable proteins) having sufficient sulphur-containing amino acids to offset such deficiency. Canola protein (i.e., isolates, hydrolysates and concentrates) is one such vegetable protein which can provide appreciable amounts of sulfur-containing amino acids to further augment the amino acid profile to deliver the necessary protein quality to the patient. Additionally, animal derived proteins are typically more abundant in sulphur-containing amino acids than vegetable proteins. Furthermore, given the potential for viscosity limitations associated with tube feeding and the need to maintain the necessary nutritional value of protein, the formula may include about 10-50% protein coming from a vegetable source.

The skilled artisan will appreciate that the protein content of the present nutritional compositions should be higher than typical long-term tube feed formulations. For example, the Recommended Dietary Allowance ("RDA") of protein for both men and women is 0.80 g of good quality protein/kg body weight/day and is based on careful analysis of available nitrogen balance studies. See, National Academy of Sciences, Institute of Medicine, Food and Nutrition Board, *Dietary Reference Intakes for Energy, Carbohydrate, Fiber, Fat, Fatty Acids, Cholesterol, Protein, and Amino Acids (Macronutrients)*, Chapter 10 (2005). In an embodiment, the present compositions provide protein to a patient in an amount of from about 1.0 to 2.5 g/kg body weight. In another embodiment, the present compositions provide protein to a patient in an amount of about 1.5 to 2.0 g/kg body weight. Accordingly, the present compositions may provide protein to a patient in an amount that is nearly twice the RDA of protein for men and women.

In an embodiment, the protein is provided in an amount to provide about 10 to about 30% energy from protein per day. In another embodiment, the protein is provided in an amount to provide from about 18% to about 35% energy from protein per day. In another embodiment, the protein is provided in an amount to provide from about 15% to about 25% energy from protein per day. Depending on the weight of the patient, and the desired amount of energy from protein to be provided to the patient, the skilled artisan will appreciate that the amounts of protein administered to a patient per day may vary. For example, the amount of protein administered per day to a patient may range from about 20 g to about 110 g. In an embodiment, the amount of protein administered per day to a patient may range from about 27 g to about 105 g. The Examples provided below further illustrate how amounts of protein may be calculated depending on the weight of the patient and the desired amount of energy from protein to be provided to the patient.

As discussed above, the nutritional compositions of the present disclosure should be hypocaloric (e.g., characterized by a low number of dietary calories) in order to provide a patient with proper nutrients but to manage weight gain without compromising the patient's health (e.g., musculoskeletal infection, wound repair, metabolic, etc.). Typically, hypocaloric diets usually provide between 1,000 and 1,200 kcal/day. Hypocaloric diets can also be defined by the energy provided per kilogram body mass. For example, less than 20 kcal/kg ideal body weight/day may be considered hypocaloric in adults. See, Dickerson et al., *Hypocaloric Enteral Tube Feeding in Critically Ill Obese Patients*, Nutrition, 18:241 (2002). Hypocaloric Enteral Tube Feeding in Critically Ill Obese Patients. These statements may be confusing since a hypocaloric diet and a hypocaloric formula are likely two different concepts. For example, a target population may have daily energy requirements of approximately 600 to 1,200 kcal/d. ESPEN guidelines define a "low energy formula" as anything below 0.9 kcal/mL. The present nutritional compositions may have caloric densities that range from about 0.3 to about 1.0 kcal/ml. In an embodiment, the nutritional compositions have a calorie density from about 0.5 to about 0.8 kcal/ml.

Osmolality is a measure of the osmoles of solute per kilogram of solvent (osmol/kg or Osm/kg). In an embodiment, the present nutritional compositions may have an osmolality that is less than or equal to 400 mOsm/kg water. In another embodiment, the present nutritional compositions have an osmolality that is less than or equal to 380 mOsm/kg water.

In an embodiment, the nutritional compositions also include curcumin. Curcumin is a component of the spice tumeric (*curcuma longa*) and is responsible for the yellow color of curry. Curcumin has specifically been shown to possess anti-inflammatory, antioxidant and anti-proteolytic properties. With regards to long-term, tube fed pediatric patients who experience profound decrements in lean body mass, curcumin may provide some attenuation of skeletal muscle proteolysis. Importantly, curcumin has been shown to antagonize the upregulation of nuclear factor-κβ (NF-κβ) and this gene is inextricably tied to initiating an intracellular signaling cascade responsible for inducing skeletal muscle atrophy during unloading conditions. See, Hunter, et al., *Disruption of Either the Nfkb1 or the Bcl3 Gene inhibits Skeletal Muscle Atrophy*, J. Clin. Invest., 114(10):1504-11 (2004).

The nutritional compositions of the present disclosure may also include a source of carbohydrates. Any suitable carbohydrate may be used in the present nutritional compositions including, but not limited to, sucrose, lactose, glucose, fructose, corn syrup solids, maltodextrin, modified starch, amylose starch, tapioca starch, corn or combinations thereof. Carbohydrates may be provided in an amount sufficient to provide from about 40% to about 60% total energy. In an embodiment, the carbohydrates are provided in an amount sufficient to provide from about 50% to about 55% total energy of the nutritional compositions.

The nutritional compositions may also include grains. The grains may include, for example, whole grains, which may be obtained from different sources. The different sources may include semolina, cones, grits, flour and micronized grain (micronized flour), and may originate from a cereal or a pseudo-cereal. In an embodiment, the grain is a hydrolyzed whole grain component. As used herein, a "hydrolyzed whole grain component" is an enzymatically digested whole grain component or a whole grain component digested by using at least an alpha-amylase, which alpha-amylase shows no hydrolytic activity towards dietary fibers when in the active state. The hydrolyzed whole grain component may be further digested by the use of a protease, which protease shows no hydrolytic activity towards dietary fibers when in the active state. The hydrolyzed whole grain component may be provided in the form of a liquid, a concentrate, a powder, a juice, a puree, or combinations thereof.

A source of fat may also be included in the present nutritional compositions. The source of fat may include any suitable fat or fat mixture. For example, the fat source may include, but is not limited to, vegetable fat (such as olive oil, corn oil, sunflower oil, high-oleic sunflower, rapeseed oil, canola oil, hazelnut oil, soy oil, palm oil, coconut oil, blackcurrant seed oil, borage oil, lecithins, and the like), animal fats (such as milk fat), or combinations thereof. The source of fat may also be less refined versions of the fats listed above (e.g., olive oil for polyphenol content). Fats may be provided in an amount sufficient to provide from about 20% to about 40% total energy. In an embodiment, the fats are provided in an amount sufficient to provide from about 25% to about 30% total energy of the nutritional compositions.

In an embodiment, the nutritional compositions further include one or more prebiotics. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof.

The nutritional compositions may further includes one or more probiotics. Non-limiting examples of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

One or more amino acids may also be present in the nutritional compositions. Non-limiting examples of amino acids include alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

The nutritional compositions may further include one or more synbiotics, and/or fatty acid components of fish oils. Non-limiting examples of fatty acid components of fish oils include docosahexaenoic acid ("DHA"), eicosapentaenoic acid ("EPA"), or combinations thereof. Other non-limiting sources of fatty acid components include krill, plant sources of omega 3, flaxseed, walnut, and algae.

One or more antioxidants may also be present in the nutritional compositions. Non-limiting examples of antioxidants include astaxanthin, carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin C, vitamin E, zeaxanthin, or combinations thereof. The antioxidants may be provided in the present nutritional compositions in an amount from about 500 to about 1,500 IU/L. In an embodiment, the antioxidants are provided in an amount of about 1,000 IU/L.

The nutritional compositions also include fiber or a blend of different types of fiber. The fiber blend may contain a mixture of soluble and insoluble fibers. Soluble fibers may include, for example, fructooligosaccharides, acacia gum, inulin, etc. Insoluble fibers may include, for example, pea outer fiber.

In embodiments of the present disclosure, methods of making a complete daily feeding tube feed composition are provided. The methods include combining a whole food component, a source of vitamins or minerals and a source of protein that provides energy from protein in an amount from about 18% to about 35% to form a mixture. The methods further include processing the mixture to form a tube feed composition that is a complete daily feeding. The processing may include blenderizing or liquefying and the whole food component may be a source of phytochemicals and/or nucleotides. The whole food component may be selected from the group consisting of a fruit, a vegetable, a meat, a grain, or combinations thereof.

In yet another embodiment, the present disclosure provides methods of improving the overall health of a tube fed pediatric patient having an underlying medical condition, including those long-term tube fed pateints. The methods include administering to a tube fed pediatric patient having an underlying medical condition a hypocaloric, complete daily feeding, tube feed formulation having a processed whole food component, a source of vitamins or minerals, and a source of protein that provides from about 18% to about 35% energy from protein. The underlying medical condition may be cerebral palsy, failure-to-thrive, neuromuscular disorders, brain injury, developmental delay, immunodeficiency, low bone density, pressure ulcers, chronic wounds, or combinations thereof.

In still yet another embodiment, the present disclosure provides methods of treating and/or preventing obesity or minimizing excessive fat-mass accretion in a long-term tube fed pediatric patient. The methods include administering to a tube fed pediatric patient that is obese, or at risk of becoming obese, a hypocaloric, complete daily feeding, tube feed formulation including a processed whole food component, a source of vitamins or minerals, and a source of protein that provides from about 18% to about 35% energy from protein.

In another embodiment, the present disclosure provides methods of promoting normal growth in a tube fed pediatric patient. The methods include administering to a tube fed pediatric patient in need of same a hypocaloric, complete daily feeding, tube feed formulation including a processed whole food component, a source of vitamins or minerals, and a source of protein that provides from about 18% to about 35% energy from protein.

In yet another embodiment, the present disclosure provides methods of maintaining metabolic homeostasis in a tube fed pediatric patient. The methods include administering to a patient in need of same a hypocaloric, complete daily feeding, tube feed formulation including a processed whole food component, a source of vitamins or minerals, and a source of protein that provides from about 18% to about 35% energy from protein.

In still yet another embodiment, the present disclosure provides methods of improving bone health in a tube fed pediatric patient on an anti-seizure medication. The methods include administering to a tube fed pediatric patient on an anti-seizure medication a hypocaloric, complete daily feeding, tube feed formulation including a processed whole food component, a source of vitamin D that provides at least 500 IU of vitamin D per 1 liter of the formulation or per 600 kcal, and a source of protein that provides from about 18% to about 35% energy from protein.

In another embodiment, methods of reducing healthcare costs for a tube fed pediatric patient are provided. The methods include providing a hypocaloric, complete daily feeding, tube feed formulation including a processed whole food component, a source of vitamins or minerals, and a source of protein that provides from about 18 to about 35% energy from protein per day. The methods further include administering the tube feed formulation to a tube fed pediatric patient having an underlying medical condition that requires medical care. The administration of the tube feed formulation improves the underlying medical condition of the patient. In an embodiment, the underlying medical condition is selected from the group consisting of cerebral palsy, failure-to-thrive, neuromuscular disorders, brain injury, developmental delay, prolonged bed rest, immobilization, paraplegia/quadraplegia, immunodeficiency, low bone density, pressure ulcers, chronic wounds, or combinations thereof.

In still yet another embodiment, methods of improving the overall health of children are provided. The methods include administering to a child a tube feed formulation including a processed whole food component, a source of vitamins or minerals, and a source of protein that provides from about 1.6 to about 3.6 g protein per kg body weight per day, wherein the formulation provides the child with about 900 to about 1,100 kcal per day. The source of protein may provide about 1.8 g protein per kg body weight, or about 3.5 g protein per kg body weight. The formulation may provide the child with about 1,000 kcal per day.

In another embodiment, methods of improving the overall health of pre-adolescents are provided. The methods include administering to a pre-adolescent a tube feed formulation including a processed whole food component, a source of vitamins or minerals, and a source of protein that provides from about 1.25 to about 2.75 g protein per kg body weight per day, wherein the formulation provides the pre-adolescent with about 1,100 to about 1,300 kcal per day. The source of protein may provide about 1.35 g protein per kg body weight, or about 2.63 g protein per kg body weight. The formulation may provide the pre-adolescent with about 1,200 kcal per day.

Nutritional compositions of the present disclosure may be beneficial when administered to patients having a variety of health concerns, as discussed above. For example, administration of nutritional compositions according to the present disclosure to children with cerebral palsy and other neuromuscular disorders (which include, for example, severe brain injuries, such as those related to premature births or developmental delays) will help the children survive longer. As these children receive long-term tube feeding including formulas with real food constituents, the children receive the benefits of food bioactives beyond the essential macro- and micronutrients required for healthy children. Additionally, feeding this type of tube-feed formulation to the children may potentially have a unique emotional appeal to caregivers and parents.

By using the improved compositions and methods of administering same, the issues associated with muscle, bone, neurological and immune health may be resolved in individuals who are either inactive or fed standard tube-feeding diets over long terms. Indeed, the improved nutritional compositions provide sufficient volume, increased protein and higher levels of certain micro- and macronutrients without providing excessive energy. Such a formulation provides an individual with a whole food component that offers the benefits of bioactives beyond the essential macro- and micronutrients.

By way of example and not limitation, the following Examples are illustrative of nutritional compositions in accordance with the present disclosure.

EXAMPLES

Hypocaloric, high-protein, blenderized tube feeding compositions in accordance with the present disclosure include a whole food component. As discussed above, the present compositions also provide high amounts of protein to a patient. For example, the compositions may provide a recommended amount of about 1.5 to 2.0 g protein/kg body weight. In an embodiment, the nutritional compositions may have caloric densities of about 0.5-0.8 kcal/ml, osmolalities that are ≤/=380 mOsm/kg water, nucleotides in an amount of about 16 mg/100 kcal, vitamin D in an amount of at least 500 IU/L, and a protein source that provides about 18 to about 35% energy from protein. It is generally known that protein provides about 4 kcal energy per gram protein.

In an example, a 10 kg (22 lb) patient consumes about 600 kcal/day. If the 10 kg patient receives protein in a range of about 1.5 to 2.0 g/kg, the patient would be expected to consume 15-20 grams of protein per day. Further, to provide 18% daily energy from protein, the 10 kg patient would be required to consume 27 g of protein per day. Accordingly, a nutritional composition in accordance with the present disclosure may include 27 g of protein.

If dietary requirements mandated that the same 10 kg patient be provided with 25% energy from protein per day, the 10 kg patient may consume a nutritional composition in accordance with the present claims that has 37.5 g of protein.

In another example, a 25 kg (55 lb) patient consumes about 1,000 kcal/day. If the 25 kg patient receives protein in a range of about 1.5 to 2.0 g/kg, the patient would be expected to consume 38-50 grams of protein per day. Further, to provide 18% daily energy from protein, the 25 kg patient would be required to consume 45 g of protein per day. Accordingly, a nutritional composition in accordance with the present disclosure may include 45 g of protein.

If dietary requirements mandated that the same 25 kg patient be provided with 25% energy from protein per day, the 25 kg patient may consume a nutritional composition in accordance with the present disclosure that has 62.5 g of protein.

In yet another example, a 40 kg (88 lb) patient consumes about 1,200 kcal/day. If the 40 kg patient receives protein in a range of about 1.5 to 2.0 g/kg, the patient would be expected to consume 60-80 grams of protein per day. Further, to provide 18% daily energy from protein, the 40 kg patient would be required to consume 54 g of protein per day. Accordingly, a nutritional composition in accordance with the present disclosure may include 54 g of protein.

If dietary requirements mandated that the same 40 kg patient be provided with 25% energy from protein per day, the 40 kg patient may consume a nutritional composition in accordance with the present disclosure that has 75 g of protein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A complete daily feeding tube feed formulation comprising:
   a processed whole food component;
   a source of vitamins or minerals; and
   a source of protein comprising animal protein and vegetable protein, the source of protein providing energy in an amount of about 18% to about 35% of the total energy of the formulation, and the tube feed formulation having a caloric density of 0.5 to 0.8 kcal per ml and an osmolality that is less than or equal to 400 mOsm/kg water.

2. The tube feed formulation according to claim 1, wherein the processed whole food component is selected from the group consisting of a processed fruit, a processed vegetable, a processed meat, a processed grain, and combinations thereof.

3. The tube feed formulation according to claim 1, wherein the proteins are selected from the group consisting of casein, caseinates, casein hydrolysate, whey, whey hydrolysates, whey concentrates, whey isolates, milk protein concentrate, milk protein isolate, and combinations thereof.

4. The tube feed formulation according to claim 1 comprising a phytonutrient selected from the group consisting of flavanoids, allied phenolic compounds, polyphenolic compounds, terpenoids, alkaloids, sulphur-containing compounds, and combinations thereof.

5. The tube feed formulation according to claim 1 comprising a nucleotide selected from the group consisting of a subunit of deoxyribonucleic acid, a subunit of ribonucleic acid, polymeric forms of DNA and RNA, and combinations thereof, wherein the nucleotide is provided in an amount of at least about 10 mg/100 kcal.

6. A method of making a tube feed composition, the method comprising:
   combining a whole food component, a source of vitamins or minerals, and a source of protein comprising animal protein and vegetable protein, to form a mixture, the source of protein providing energy in an amount of about 18% to about 35% of the mixture; and
   processing the mixture to form a tube feed composition that is a complete daily feeding, and the tube feed formulation having a caloric density of 0.5 to 0.8 kcal per ml and an osmolality that is less than or equal to 400 mOsm/kg water.

7. The method according to claim 6, wherein the whole food component is selected from the group consisting of a fruit, a vegetable, a meat, a grain, and combinations thereof.

8. The method according to claim 6, wherein the processing comprises blenderizing.

9. The method according to claim 6, wherein the whole food component is a source of phytochemicals and/or nucleotides.

10. The method according to claim 6, wherein the source of vitamins or minerals comprises a source of vitamin D that provides at least 500 IU.

11. The method according to claim 6, wherein the tube feed formulation comprises nucleotides in an amount of at least about 10 mg/100 kcal.

12. A method of improving the overall health of a tube fed pediatric patient having an underlying medical condition, the method comprising:
administering to a tube fed pediatric patient having an underlying medical condition a hypocaloric, complete daily feeding, tube feed formulation comprising a processed whole food component, a source of vitamins or minerals, and a source of protein that provides about 18% to about 35% energy from protein, and the tube feed formulation having a caloric density of 0.5 to 0.8 kcal per ml and an osmolality that is less than or equal to 400 mOsm/kg water.

13. The method according to claim 12, wherein the underlying medical condition is selected from the group consisting of cerebral palsy, failure-to-thrive, neuromuscular disorders, brain injury, developmental delay, immunodeficiency, low bone density, pressure ulcers, chronic wounds, and combinations thereof.

14. The method according to claim 12, wherein the source of vitamins or minerals comprises a source of vitamin D that provides at least 500 IU of vitamin D per liter of the formulation or per 600 kcal.

15. The method according to claim 12, wherein the tube feed formulation comprises nucleotides in an amount of at least about 10 mg/100 kcal.

16. The tube feed formulation according to claim 1, wherein the vegetable protein comprises a plant-based protein selected from the group consisting of pea protein concentrate, pea protein isolate, and a combination thereof.

17. The method according to claim 6, wherein the vegetable protein comprises a plant-based protein selected from the group consisting of pea protein concentrate, pea protein isolate, and a combination thereof.

18. The method according to claim 12, wherein the protein comprises a plant-based protein selected from the group consisting of pea protein concentrate, pea protein isolate, and a combination thereof.

19. The tube feed formulation according to claim 1, wherein the animal protein comprises chicken and milk protein.

* * * * *